United States Patent
O'Donohue et al.

(10) Patent No.: US 7,561,268 B2
(45) Date of Patent: Jul. 14, 2009

(54) EVAPORATIVE LIGHT SCATTERING DETECTOR

(75) Inventors: Stephen John O'Donohue, Shrewsbury (GB); Nathan James Wrench, Bishops Castle (GB); Paul Emil Claes, Shrewsbury (GB)

(73) Assignee: Polymer Laboratories Ltd, Shropshire (GB)

( * ) Notice: Subject to any disclaimer, the term of this patent is extended or adjusted under 35 U.S.C. 154(b) by 435 days.

(21) Appl. No.: 10/546,753

(22) PCT Filed: Feb. 24, 2004

(86) PCT No.: PCT/GB2004/000767

§ 371 (c)(1),
(2), (4) Date: May 30, 2006

(87) PCT Pub. No.: WO2004/077047

PCT Pub. Date: Sep. 10, 2004

(65) Prior Publication Data

US 2006/0238744 A1    Oct. 26, 2006

(30) Foreign Application Priority Data

Feb. 25, 2003    (GB) .................................. 0304253.8

(51) Int. Cl.
*G01N 15/06* (2006.01)
(52) U.S. Cl. ...................................................... 356/337
(58) Field of Classification Search .......... 356/337–343
See application file for complete search history.

(56) References Cited

U.S. PATENT DOCUMENTS

| 4,628,048 | A | 12/1986 | Acker et al. |
| 4,958,529 | A | 9/1990 | Vestal |
| 4,990,740 | A | 2/1991 | Meyer |
| 5,098,657 | A | 3/1992 | Blackford et al. |
| 5,374,396 | A | 12/1994 | Blackford et al. |
| 2001/0001575 | A1 * | 5/2001 | Anderson et al. ........... 356/337 |

FOREIGN PATENT DOCUMENTS

| EP | 1 275 961 A1 | 1/2003 |
| WO | WO 98/10279 | 3/1998 |

OTHER PUBLICATIONS

Yang and Koropchak, , "Condensation Nucleation Light Scattering Detection with Microbore Liquid Chromatography for Lipid Analysis", *J. Microcolumn Separations.*, vol. 12(4), pp. 204-210, (2000).

* cited by examiner

*Primary Examiner*—Tarifur Chowdhury
*Assistant Examiner*—Tara S Pajoohi
(74) *Attorney, Agent, or Firm*—Bella Fishman

(57) ABSTRACT

An improved evaporative light scattering detector apparatus for volatile samples is provided. Conventionally incomplete evaporation of the mobile phase (solvent) cannot be achieved for volatile samples as solvent cannot be fully removed at low temperature because the vapor becomes saturated. At higher temperatures the samples evaporate without forming an aerosol. By adding a dry evaporator gas to the sample before entering a drift tube avoids saturation of the vapor and permits complete evaporation of the solvent at low temperatures.

17 Claims, 3 Drawing Sheets

EVAPORATIVE LIGHT SCATTERING DETECTOR

CROSS REFERENCE TO RELATED APPLICATIONS

This application is a 35USC §371 national Stage application of PCT Application No. GB2004/000767 field Feb. 24, 2004, which claims the benefit under 35 USC § 119(a) of United Kingdom Application No. 0304253.8 field Feb. 25, 2003. The disclosure of each of the prior applications is considered part of and is incorporated by reference in the disclosure of this application.

FIELD OF THE INVENTION

The present invention relates to an improved evaporator system for use in evaporative light scattering detectors.

BACKGROUND OF THE INVENTION

Evaporative Light Scattering (ELS) detection is a method of detecting samples that have been previously separated by chromatography methods such as High Performance Liquid Chromatography (HPLC), Gel Permeation Chromatography (GPC) and Gradient Polymer Elution Chromatography (GPEC). Evaporative Light Scattering Detection is preferably used when the samples to be analysed are less volatile than the mobile phase (solvent). The technique is useful in the analysis of many substances including carbohydrates, lipids and fatty acids, underivatised amino acids, pharmaceutical compounds, surfactants, polymer blends and copolymers.

ELS detection is a three stage process:
1. Nebulization of the chromatography eluent, either as mobile phase (solvent) or eluent containing a less volatile sample, to form an aerosol or plume of uniform droplets. Most commercial ELS detectors produce this plume by introducing the eluent to a high velocity stream of nitrogen or other inert gas in a pneumatic nebulizer, but it can also be achieved by methods such as passing the eluent through a high frequency vibrating capillary or impacting it upon an oscillating plate or 'horn' (ultrasonic nebulizer).
2. Evaporation of the mobile phase to generate a plume of non-volatile solute (sample) particles. This occurs in a heated tube commonly referred to as a 'drift tube' or 'evaporator'.
3. Optical detection of the light scattered by the solute particles from an incident light beam. In principle, the detector response is proportional to the mass of solute passing through the light beam.

Those skilled in the art will readily appreciate that any mobile phase remaining as un-evaporated droplets in the plume will produce an undesirable response from the detector in the form of 'baseline noise' as it passes through the light beam. In order to minimise this effect it is common practice to remove from the plume the largest droplets (which are the most difficult to evaporate). This is most commonly achieved by utilising an impact trap; the simplest form of which is that of a drift tube of smaller diameter than the natural form of the aerosol plume produced by the nebulizer. The large droplets are less mobile and more "ballistic" in nature than the small droplets so impact upon the walls of the drift tube. Once impacted upon the walls the liquid can either be channelled to waste or boiled off by heating the drift tube above the boiling point of the liquid. Alternative designs of impact trap in common use include drift tubes with bends or changes in cross section or balls, plates or flaps in the immediate path of the primary aerosol.

It can be seen therefore that to the three principal stages of Evaporative Light Scattering Detection (ESLD) a fourth has been added; the removal of the larger droplets and the selection of the remaining portion of the nebulized plume for detection. This stage is employed in every current commercially available ELSD.

Hereinafter the following definitions are used:
Primary aerosol The mixture of eluent droplets and nebulizing gas as formed by the nebulizer.
Secondary aerosol The portion of the mixture of eluent droplets and nebulizing gas remaining after the impact trap and physically selected for evaporation.
Tertiary aerosol The mixture of sample residue and gas exiting the evaporator after drying has taken place.

The response of the ELSD is dependent on the concentration of sample droplets or particles in the tertiary aerosol, relative to the volume of gas. In order to increase the sensitivity much effort has been made to reduce the quantity of gas required by the nebulizer to produce a stable aerosol without diluting the sample.

The vapour loading in the plume is a function of nebulizer temperature. Higher nebulizer temperatures permit greater sample loading of the plume resulting in more complete evaporation and greater sample density at the detector. The gas immediately after nebulization will be saturated, therefore complete drying of the sample droplets and vaporization of the mobile phase in the secondary aerosol will be impossible unless the temperature of the gas is subsequently raised. This temperature rise will increase the saturation vapour pressure of the eluent in the gas sufficiently to absorb all the liquid in the droplets. For this reason, the drift tube in an ELSD is normally heated.

Depending on the design of the instrument, the efficiency of the nebulizer and the volatility of the eluent, it is frequently necessary to operate with evaporator temperatures in excess of the boiling point of the eluent. As an example, the PL-ELS 1000 (manufactured by Polymer Laboratories Ltd, Church Stretton, Shropshire, UK) features a nebulizer of a highly efficient type, requiring nebulizer gas flow rates of the order of only 1 standard Liter per minute (SLM) to produce a stable primary aerosol with eluent flow rates of up to 2 ml/min. In this circumstance (using the example of a water-based eluent) it is generally necessary (in order to maximize the signal to noise ratio) to operate with the temperature of the evaporator set to 120° C.

However, it is frequently not desirable to raise the temperature as this will cause evaporation or degradation of volatile samples and hence loss of sensitivity of the detector for these samples.

SUMMARY OF THE INVENTION

An object of the invention is to overcome the incomplete eluent evaporation problem of volatile or temperature sensitive samples that require low temperature evaporation. This is achieved by introducing an "evaporative gas" to the secondary aerosol before entering the drift tube. The evaporative gas is dry and permits complete evaporation of the eluent droplets associated with the plume. The addition of a carefully controlled stream of dry gas to the secondary aerosol enables complete evaporation of the eluent to take place without raising the temperature, thus increasing sensitivity for volatile samples and reducing noise (caused by larger droplets which would not otherwise be evaporated to dryness during the time of flight). This is the essence of this invention.

Additional gas injections have been featured on previous ELSDs and similar instruments. However, we have found that the addition must be made to the secondary aerosol in order to assist evaporation of the mobile phase, and this represents an improvement in the state of the art.

A study of the literature and prior art reveals that other uses of nebulization in instrumentation is to produce uniform particles or droplets, and in some cases the elimination of solvent is not as critical in the application as compared to the ELSD the focus being generally on the production of uniform particle size. U.S. Pat. No. 4,628,048 is an example of this, where nebulization is used to manufacture uniform spheroid catalyst beads. The ELSD however demands not only a uniform particle distribution but, also for optimum performance, an efficient means of removing any spurious larger ballistic particles together with the removal of solvent from the solute droplets and complete evaporation of droplets when no solute is present.

The Sedex 75 ELSD (manufactured by S.E.D.E.R.E., France) features a concentric sheath of additional gas enclosing the tertiary aerosol to assist in the reduction of turbulence as the aerosol passes through the optical chamber. This gas sheath reduces the risk of condensation forming on the lenses and optical components and reduces peak-top noise (a function of plume instability) but does not assist in the evaporation of the mobile phase, as it does not mix with the aerosol.

US patent publication no. US 2001/0001575A1 discloses a system where extra gas is injected into a heated nebulization chamber. However, this will become saturated with vapour evaporating from the chamber walls and with liquid droplets borne on the primary aerosol. The principal benefit of a 'sweep gas inlet' immediately next to the nebuliser is in the relief of the vacuum formed by the high velocity nebulization process. This reduces mixing in the nebuliser chamber and can benefit the mass transport through the system, but will have only a very marginal benefit to the concentration of sample particles in the tertiary aerosol (and therefore to the response of the detector). An advantage is only observed once the majority of the eluent has impacted on the walls of the nebulization chamber and been channelled to waste.

A related instrument that also includes a secondary gas stream is the Condensation Nucleation Light Scattering Detector (CNLSD) (J. A. Koropchak and X. Yang J. Microcolumn Separations 12(4) 204-210 (200)). In this device, a nebuliser is used to produce an aerosol, which is evaporated to dryness using a combination of impact traps and heat, as in a conventional ELSD. In CNLSD a condensation phase is added, where the aerosol passes through a cooled chamber in order to remove much of the solvent vapor. After these stages, the (tertiary) aerosol undergoes an additional stage before flowing into the optical chamber. The tertiary aerosol is mixed with saturated butanol vapor in a 'growth condenser' in order to increase the size of the sample particles through condensation nucleation. This increase in particle size greatly benefits the light scattering efficiency and hence is reported to improve the sensitivity of the system.

The additional gas stream (butanol vapor) in a CNLSD is thus performing a very different function to our evaporator gas invention. In a CNLSD the fully saturated additional gas is added to a 'dry' tertiary aerosol in order to increase the size of the sample particles. Our invention adds a stream of unsaturated (dry) gas to a 'wet' secondary aerosol in order to evaporate the unwanted solvent to dryness. Our invention would no doubt benefit a CNLSD as it would improve the function of the nebulizer and evaporator stages, providing a dry aerosol at low temperatures before the addition of the butanol vapor.

Another related instrument that includes a secondary gas stream is the Evaporative Electrical Detector (EED) as manufactured by TSI Inc and covered by U.S. Pat. Nos. 5,098,657 and 5,374,396. In this detector a nebulizer, impact trap and drift tube arrangement is used to produce a dry (tertiary) aerosol which then flows through a subsonic orifice to form a turbulent jet. Unipolar ions from a corona discharge at a platinum needle tip are swept by a flow of filtered air through a second subsonic orifice, forming a turbulent jet opposing the aerosol particle jet. The mixing of the two turbulent jets, combined with diffusion, causes rapid charging of the aerosol, which leaves the mixing chamber through a lateral port and flows to the detector (in this case an Electrical Charge Detector rather than a Light Scattering Detector).

The purpose of the secondary gas inlet in the case of the EED is to carry the unipolar ions to the aerosol and so enable efficient charging of the particles therein. The additional gas plays no part in the evaporation of the unwanted background solvent as it is added to the 'dry' tertiary aerosol. Again, it is possible that our invention would benefit the operation of an EED, as it would improve the evaporation efficiency of the nebulizer and evaporator stages, providing a dry aerosol at low temperatures before the particle charging and detection stages.

An intra-microspray ICP torch (U.S. Pat. No. 4,990,740) for use in conjunction with spectrographic analysis also uses additional gas injections post nebulization. However, in this technique two gases are introduced into the tertiary aerosol at the end of the torch. Each of the gases must be both inert and ionizable the first used as a plasma gas within the ICP torch and the second as coolant around the torch.

Thus, in a first aspect, the present invention provides a light scattering detection apparatus comprising a nebulizer and means for introduction of an "evaporator gas" into the post nebulization drying stage in the secondary aerosol. Suitably, the apparatus of the first aspect is for use with chemical moieties in solution or particles in liquids, and operates over a temperature range from sub-ambient to 120° C.

The present invention provides an evaporative light scattering detection apparatus comprising a nebulizer and means for introduction of additional (evaporator) gas into the secondary aerosol for the purpose of evaporating solvent from the solute droplets and complete evaporation of the droplets when no solute is present. Preferably, this evaporator gas is introduced into the secondary aerosol downstream of the nebulizer. It is advantageous, but not necessary to introduce this evaporator gas into the secondary aerosol after any chambers or bends which remove excess droplets or ballistic particles.) Preferably, the evaporator gas is nitrogen, however other gases maybe used.

Generally, the apparatus of the present invention forms part of a "conventional" ELSD system and thus further comprises optical detection means for detection of an incident light beam scattered by solute particles.

The present invention provides advantages for:
(i) the use of the apparatus of the invention in detection devices for continuous monitoring of chemical moieties or particles in liquids.
(ii) the use of the apparatus of the invention in detection devices for chromatography applications for chemical compounds or particles, whether as mixtures or single components

DETAILED DESCRIPTION OF THE INVENTION

The response of the ELSD is dependent on the concentration of sample droplets or particles in the tertiary aerosol, relative to the volume of gas. In order to increase the sensitivity much effort has been made to reduce the quantity of gas required by the nebulizer to produce a stable aerosol without diluting the sample.

Modelling of the physical processes occurring in the nebulizer indicates that the carrier gas will become saturated with eluent vapour both during nebulization itself and due to subsequent evaporation of eluent off the walls of the nebulization chamber. This is the first time that the ability of the gas (in the primary aerosol) to absorb vapour has been calculated and reported in respect of an ELSD.

Figure 1:
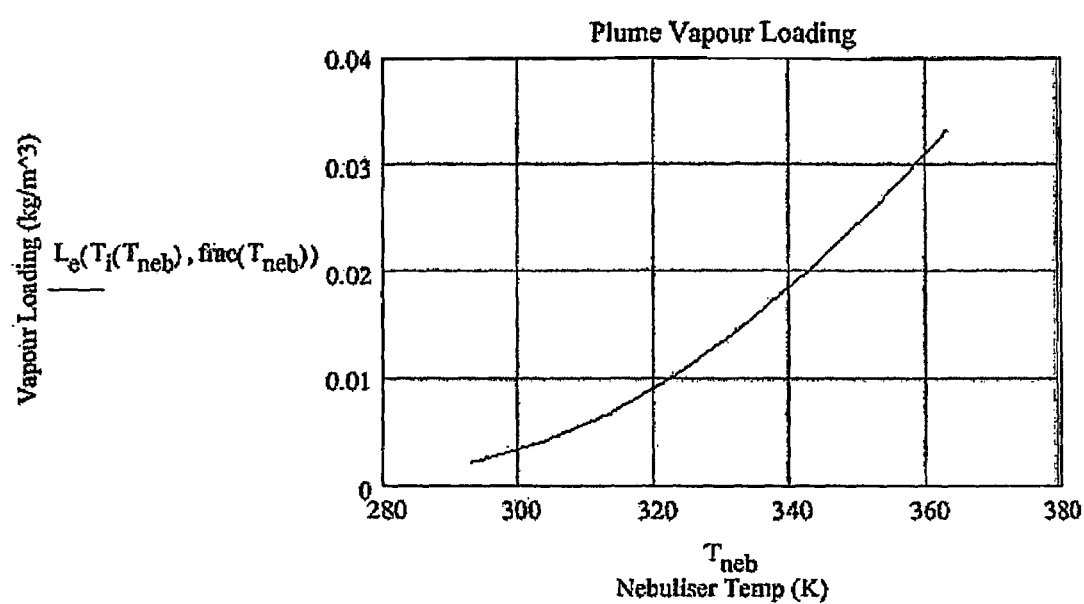
FIG. 1 is a plot of the vapor loading of a solute as a function of the nebulizer temperature.

The vapor loading in the plume is calculated as a function of nebulizer temperature as plotted in FIG. 1. This illustrates that the gas immediately after nebulization will be saturated, therefore complete drying of the sample droplets and vaporization of the mobile phase in the secondary aerosol will be impossible unless the temperature of the gas is subsequently raised. This temperature rise will increase the saturation vapour pressure of the eluent in the gas sufficiently to absorb all the liquid in the droplets. For this reason, the drift tube in an ELSD is normally heated.

Figure 2:
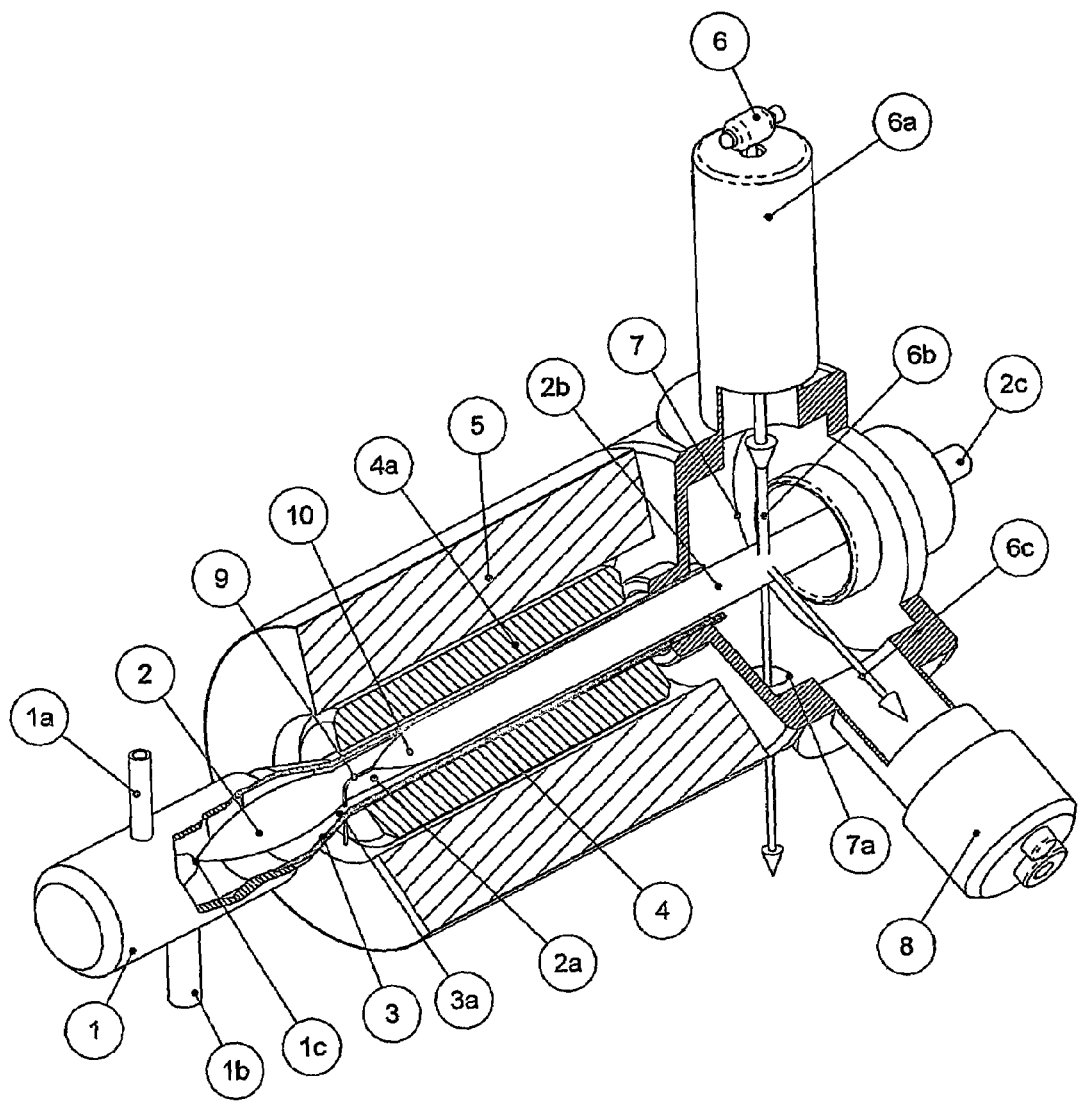
FIG. 2 is perspective drawing of the improved ELSD of the present invention.

A preferred embodiment of the invention will now be described with reference to FIG. 2. The chromatography eluent is connected to the nebulizer (1) and directed through the nebulizer needle (1c). The nebulizing gas (preferably Nitrogen) is connected to the gas inlet port (1a) and impacts the chromatography eluent to form an aerosol of droplets—the primary aerosol (2). The nebulizer (1) maybe maintained at a constant temperature by means of a heater and control circuit (not shown).

The primary aerosol (2) flows into the nebulization chamber (3). Larger droplets in the aerosol, being less mobile than the small droplets, are unable to negotiate the entrance to the drift tube (3a), so impact on the walls of the nebulization chamber (3) and drain away through the waste port (1b). The resulting secondary aerosol (2a) consists of all the nebulizer gas and that portion of the chromatography eluent forming small and mobile droplets. With some eluents, the quantity of liquid, which is found in the secondary aerosol, will be approximately one-tenth to one-fifth of the total supplied to the nebulizer.

At this point, the gas in the secondary aerosol (2a) will be nearing or at saturation. Evaporation of the remaining droplets will be inhibited without an increase in temperature—which could be undesirable if semi-volatile or volatile samples are being analysed. In order to aid evaporation of the eluent therefore, a second supply of gas (preferably Nitrogen) is connected to the inlet port (9) and allowed to flow into the drift tube (4). This second gas supply mixes with the secondary aerosol (10) and flows through the drift tube (4).

The drift tube (4) is preferably maintained at a constant temperature in a temperature-controlled block (4a), which is insulated (5) to reduce thermal effects. The addition of a dry gas supply is sufficient to evaporate the mobile phase from the solute droplets and the droplets of the mobile phase when no solute is present. At the exit to the drift tube (4) the tertiary aerosol (2b) will contain only droplets or particles of analytes which are less volatile than the mobile phase or eluent.

For good detection of highly volatile compounds it is desirable to cool the evaporator to preserve the sample droplets in the aerosol. In this case since the primary aerosol is cooled due to adiabatic cooling during nebulization, sufficient evaporation of the eluent droplets can only be achieved by the addition of a dry gas injection into the secondary aerosol.

Inside the optical chamber (7) the tertiary aerosol intersects a light beam (6b) produced from a light source (6) and collimated or focused by a system of lenses and apertures (6a). Any residual droplets or particles in the tertiary aerosol will scatter light. The scattered light is detected at the photodetector (8), which produces an output signal proportional to the intensity of scattered light and therefore proportional to the concentration of droplets (sample) in the aerosol.

Any light not scattered by sample droplets is collected by a light trap (7a). At the exit to the optical chamber the aerosol (2c) flows to exhaust.

The invention will now be described by way of the following example, which should not be construed as in any way limiting the scope of the invention.

In this experiment, the PL-ELS 1000 (Manufactured by Polymer Laboratories Ltd.) was used to analyse a mixture of four volatile samples.

Column: Adsorbosil C18 5μ, 150×4.6 mm
Eluent A: 0.1% TFA, Water
Eluent B: 0.1% TFA, ACN
Gradient: 60-90% B in 5 minutes
Flow rate: 1.0 mL/min
Sample: 1.0 mg/mL mix of acetanilide, indapamide, ibupfrofen, dibutyl phthalate in 50% ACN, 50% water Although the samples are volatile it was not possible to use low temperatures without un-evaporated mobile phase giving excessive baseline noise and offset. The lowest temperature settings that could be used were as follows:

a. Conditions: Drift tube 80° C., nebuliser 80° C., nebulizer gas flow 1.0 SLM

Figure 3A:
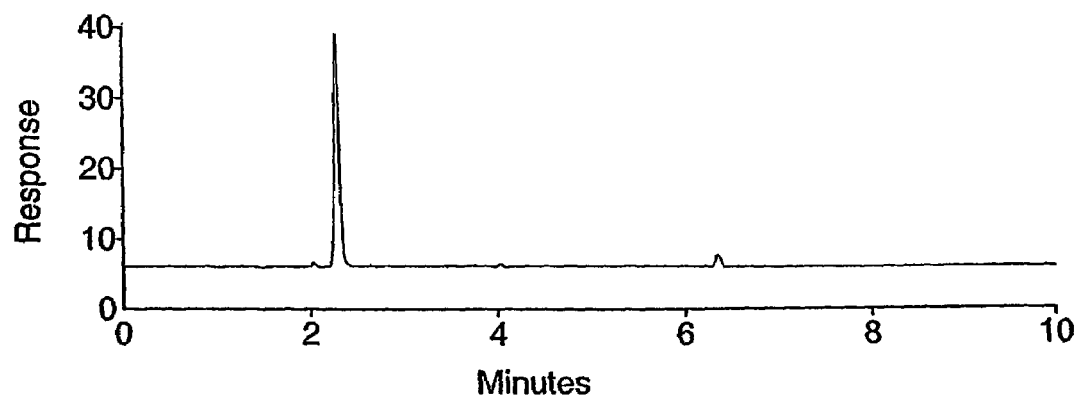
FIG. 3a is a trace from a model 1000 of Polymer Laboratories Evaporative Light Scattering detector of a liquid chromatograph output of a mixture of four analytes operating with the nebulizer and drift tube at 80° C. and nebulizer gas flow 1.0 SLM and no evaporator gas injection.

The trace is shown in FIG. 3(a) and, as can be seen, using the standard PL-ELS 1000 under standard conditions only one of the solutes (indapamide, peak 2) was detected with any real response.

Figure 3B:
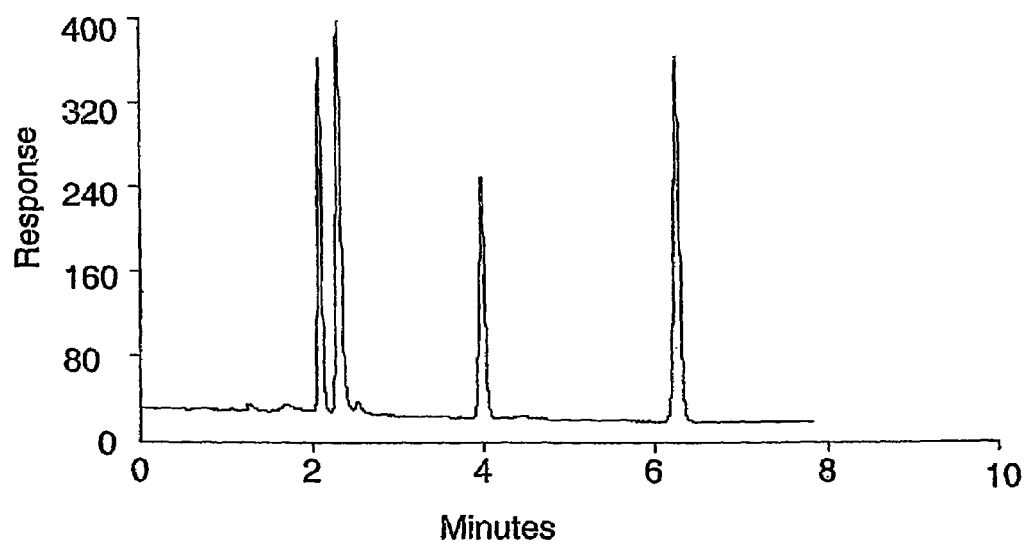
FIG. 3b is a trace from the instrument and sample of FIG. 3a except the nebulizer and drift tube were approximately 20° C., and nebulizer gas flow of 1.0 SLM and evaporator gas injection of 1.0 SLM.

In this invention, the addition of a controlled quantity of dry gas to the secondary aerosol enables evaporation of the mobile phase without an increase in the temperature of the evaporator. Using a modified PL-ELS 1000 with the addition of a gas inlet port at the entrance to the evaporator it was possible to perform the same analysis with the nebulizer and evaporator heaters switched off. The system was therefore operating at a room temperature of about or less than 20° C., without baseline noise becoming excessive, the actual conditions used were:

Conditions: Drift tube heater off, nebulizer heater off, nebuliser gas flow 1.0 SLM, evaporator gas injection 1.0 SLM The trace is shown in FIG. 3(b) and all four components can be detected with significantly improved signal to noise ratios. Detection of the second solute (indapamide) has been improved by an order of magnitude, and detection of the other three solutes has improved by approximately 300×.

The invention claimed is:

1. A light scattering detection apparatus comprising:
   a nebulizer having a first inlet port for receiving chromatographic eluent with sample material and solvent, and a second inlet port for receiving nebulizing gas, said nebulizer producing primary aerosol of different size droplets from said eluent;

a nebulization chamber coupled to said nebulizer for receiving the primary aerosol of different size droplets and nebulizing gas and for separating droplets of primary aerosol into larger and smaller sizes of droplets partially drying thereof, the droplets of smaller sizes and the nebulizing gas forming a secondary aerosol; and a drift tube having a first inlet port connected to the nebulization chamber for receiving the secondary aerosol, and a second inlet port for receiving an evaporator gas into the drift tube for mixing with the secondary aerosol, wherein the evaporator gas allows for drying of the secondary aerosol by evaporating a solvent from the droplets to form a tertiary aerosol of dried aerosol droplets.

2. The light scattering detection apparatus as claimed in claim 1, wherein said nebulization chamber provides an impact region for removing the larger droplets from said primary aerosol produced by the nebulizer.

3. The light scattering detection apparatus as claimed in claim 2, wherein said nebulization chamber contains a waste port for the removal of said larger droplets from the nebulization chamber.

4. The light scattering detection apparatus as claimed in claim 1, wherein said nebulization chamber provides heating means to control its temperature.

5. The light scattering detection apparatus as claimed in claim 1, wherein said evaporator gas is nitrogen.

6. The light scattering detection apparatus as claimed in claim 1, wherein said evaporator gas is less than saturated with vapor.

7. The light scattering detection apparatus as claimed in claim 1, wherein the evaporator gas is introduced substantially downstream from the nebulizer.

8. The light scattering detection apparatus as claimed in claim 1, wherein means are provided to cool the drift tube.

9. The light scattering detection apparatus as claimed in claim 1, wherein means are provided to heat the drift tube.

10. The light scattering detection apparatus as claimed in claim 1, wherein the evaporator gas is introduced into the secondary aerosol after the nebulization chamber.

11. The light scattering detection apparatus as claimed in claim 1, wherein the evaporator gas is introduced into the secondary aerosol after any post nebulization impactors.

12. The light scattering detection apparatus as claimed in claim 1, wherein the evaporator gas is introduced into the secondary aerosol after any bends or chambers designed into the apparatus, whish act as ballistic traps.

13. The light scattering detection apparatus as claimed in claim 1, wherein the evaporator gas is introduced into the secondary aerosol before complete evaporation of the solvent.

14. The light scattering detection apparatus as claimed in claim 1, which further comprises optical detection means for detection of an incident light beam scattered by solute particles, particles in the tertiary aerosol.

15. The light scattering detection apparatus as claimed in claim 1, is a detector utilized in chromatography of chemical moieties or mixtures thereof or particles or mixtures thereof.

16. The light scattering detection apparatus as claimed in claim 1, is a detector utilized for continuous monitoring of particles in liquids.

17. The light scattering detection apparatus as claimed in claim 1, further comprising a cooled drift tube.

* * * * *